US009579347B2

(12) United States Patent
Pereira et al.

(10) Patent No.: US 9,579,347 B2
(45) Date of Patent: Feb. 28, 2017

(54) METHODS FOR ENHANCING THE EFFECT OF EGCG ON MITIGATING SKELETAL MUSCLE LOSS (71) Applicant: ABBOTT LABORATORIES, Abbott Park, IL (US)

(72) Inventors: Suzette Pereira, Westerville, OH (US); Sean Garvey, Columbus, OH (US); Neile Edens, Columbus, OH (US)

(73) Assignee: ABBOTT LABORATORIES, Abbott Park, IL (US)

( * ) Notice: Subject to any disclaimer, the term of this patent is extended or adjusted under 35 U.S.C. 154(b) by 0 days.

(21) Appl. No.: 14/433,538

(22) PCT Filed: Oct. 4, 2013

(86) PCT No.: PCT/US2013/063519
§ 371 (c)(1),
(2) Date: Apr. 3, 2015

(87) PCT Pub. No.: WO2014/055905
PCT Pub. Date: Apr. 10, 2014

(65) Prior Publication Data
US 2015/0265650 A1 Sep. 24, 2015

Related U.S. Application Data (60) Provisional application No. 61/709,682, filed on Oct. 4, 2012.

(51) Int. Cl.
*A61K 33/30* (2006.01)
*A23L 33/00* (2016.01)
*A61K 31/353* (2006.01)
*A61K 38/01* (2006.01)
*A61K 35/20* (2006.01)
*A61K 36/48* (2006.01)
*A23L 2/66* (2006.01)
*A61K 9/00* (2006.01)
*A61K 36/82* (2006.01)
*A61K 38/39* (2006.01)

(52) U.S. Cl.
CPC ............... *A61K 33/30* (2013.01); *A23L 2/66* (2013.01); *A23L 33/105* (2016.08); *A23L 33/16* (2016.08); *A23L 33/17* (2016.08); *A23L 33/175* (2016.08); *A23L 33/19* (2016.08); *A23L 33/195* (2016.08); *A23L 33/40* (2016.08); *A61K 9/0095* (2013.01); *A61K 31/353* (2013.01); *A61K 35/20* (2013.01); *A61K 36/48* (2013.01); *A61K 36/82* (2013.01); *A61K 38/011* (2013.01); *A61K 38/018* (2013.01); *A61K 38/39* (2013.01); *A23V 2002/00* (2013.01)

(58) Field of Classification Search
None
See application file for complete search history.

(56) References Cited

U.S. PATENT DOCUMENTS

| 5,455,059 A | * | 10/1995 | McFeaters | A23G 1/56 426/578 |
| 6,509,054 B1 | * | 1/2003 | Haddad | A23L 1/3002 426/478 |
| 7,026,298 B2 | | 4/2006 | Phillips et al. | |
| 7,914,829 B2 | | 3/2011 | Jacquet | |
| 2002/0122835 A1 | | 9/2002 | Bucci et al. | |
| 2004/0198673 A1 | | 10/2004 | Chen et al. | |
| 2005/0003068 A1 | | 1/2005 | Kester et al. | |
| 2005/0260302 A1 | * | 11/2005 | Prosise | A23L 1/1643 426/72 |
| 2006/0188548 A1 | | 8/2006 | Mattson et al. | |
| 2007/0015686 A1 | | 1/2007 | Heuer et al. | |
| 2008/0193601 A1 | | 8/2008 | Nasser | |
| 2009/0035440 A1 | | 2/2009 | Velikov | |
| 2009/0176312 A1 | * | 7/2009 | Selinfreund | B01L 7/52 436/164 |
| 2009/0214680 A1 | | 8/2009 | Giuliano et al. | |
| 2009/0263367 A1 | | 10/2009 | Foley | |

(Continued)

FOREIGN PATENT DOCUMENTS

EP 1712140 10/2006
FR 2882896 9/2006

(Continued)

OTHER PUBLICATIONS

Yayabe, Industrial application of tea extracts, http://www.ocha-festival.jp/archive/english/conference/ICOS2001/files/PROC/III-080.pdf, retrieved online Mar. 30, 2016.*
RateTea, Calories in Tea—With and Without Milk or Sugar, http://ratetea.com/topic/calories-in-tea/91/, Jul. 2015.*
Editors Web, Essential Nutrients—water, proteins, carbohydrates, fats, vitamins and minerals, http://www.editorsweb.org/nutrition/essential-nutrients.htm, retrieved online on Mar. 23, 2016.*
International Search Report and Written Opinion for PCT/US2013/063394 mailed Feb. 7, 2014.

(Continued)

*Primary Examiner* — Jennifer A Berrios
(74) *Attorney, Agent, or Firm* — Porter Wright Morris & Arthur LLP (57) ABSTRACT Disclosed herein are methods for enhancing the efficacy of epigallocatechin gallate ("EGCg") in mitigating skeletal muscle loss in a subject. Providing EGCg to a subject in a nutritional composition reduces muscle protein degradation, thereby mitigating skeletal muscle loss in the subject. The combination of EGCg with zinc in a nutritional composition enhances the mitigating effect that EGCg has on muscle loss. Specifically, when used in combination, a nutritional composition containing both EGCg and zinc requires less EGCg to obtain the same mitigating effect that occurs in the same nutritional composition containing EGCg but no zinc.

20 Claims, 2 Drawing Sheets

(56) References Cited

U.S. PATENT DOCUMENTS

| | | | |
|---|---|---|---|
| 2009/0281174 A1* | 11/2009 | Ota | A23L 1/3002 514/456 |
| 2009/0297640 A1 | 12/2009 | Gardiner et al. | |
| 2010/0129467 A9 | 5/2010 | Albritton et al. | |
| 2010/0179112 A1* | 7/2010 | Rathmacher | A23L 1/30 514/167 |
| 2011/0305799 A1 | 12/2011 | DeWille et al. | |

FOREIGN PATENT DOCUMENTS

| | | | |
|---|---|---|---|
| JP | 2006188436 | | 12/2004 |
| JP | 2011225475 | | 11/2011 |
| JP | 2012180331 | * | 9/2012 |
| JP | 2012180347 | | 9/2012 |
| WO | 00/00183 | | 1/2000 |
| WO | 2007042271 | | 4/2007 |
| WO | 2008037740 | | 4/2008 |
| WO | 2008115563 | | 9/2008 |
| WO | 2011011252 | | 1/2011 |
| WO | 2012006074 | | 1/2012 |
| WO | 2012097061 | | 7/2012 |

OTHER PUBLICATIONS

International Preliminary Report on Patentability for PCT/US2013/063394 dated Apr. 7, 2015.
International Search Report and Written Opinion for PCT/US2013/063519 mailed Jan. 3, 2014.
International Preliminary Report on Patentability for PCT/US2013/063519 dated Apr. 7, 2015.
Communication pursuant to Rules 161 and 162 in EP 13776697.8 dated May 18, 2015.
Altun, et al. "Muscle wasting in aged, sarcopenic rats is associated with enhanced activity of the ubiquitin proteasome pathway," J Biol Chem., vol. 285(51), pp. 39597-39608, Dec. 17, 2010.
Clavel, et al. "Atrophy-related ubiquitin ligases, atrogin-1 and MuRF1 are up-regulated in aged rat Tibialis Anterior muscle," Mech Ageing Dev., vol. 127(10), pp. 794-801, Oct. 2006.
Dorchies, et al. "Green tea extract and its major polyphenol (−)-epigallocatechin gallate improve muscle function in a mouse model for Duchenne muscular dystrophy," American Journal of Physiology, vol. 290 (2), pp. C616-C625 Feb. 1, 2006.
Eley, et al. "Signaling pathways initiated by beta-hydroxy-beta-methylbutyrate to attenuate the depression of protein synthesis in skeletal muscle in response to cachectic stimuli," Am J Physiol Endocrinol Metab., vol. 293(4), pp. E923-E931, Oct. 2007.
Glass, "Signaling pathways perturbing muscle mass," Curr. Opin. Clin. Nutr.and Metab Care, vol. 13(3), pp. 225-229, May 2010.
Hao, et al. "β-Hydroxy-β-methylbutyrate reduces myonuclear apoptosis during recovery from hind limb suspension-induced muscle fiber atrophy in aged rats," Am J Physiol Regul Integr Comp Physiol., vol. 301(3), pp. R701-R715, Sep. 2011.
Hepple, et al. "Caloric restriction optimizes the proteasome pathway with aging in rat plantaris muscle: implications for sarcopenia," Am J Physiol Regul Integr Comp Physiol., vol. 295(4); pp. R1231-R1237, Oct. 2008.
Kagaya, et al. "Enhancing Effect of Zinc on Hepatoprotectivity of Epigallocatechin Gallate in Isolated Rat Hepatocytes", Biological and Pharmaceutical Bulletin, vol. 25(9), pp. 1156-1160, Sep. 2002.
Lecker, "Given the science on malnutrition, how does the clinician respond? Practical lessons for and application to the dialysis patient," Clin J Am Soc Nephrol., vol. 4 Suppl 1, pp. S64-S70, Dec. 2009.
Raue, et al. "Proteolytic gene expression differs at rest and after resistance exercise between young and old women," J Gerontol A Biol Sci Med Sci., vol. 62(12), pp. 1407-1412, Dec. 2007.
Rich chocolate ready to drink nutrition basics, available at http://glucema.com/diabetes-shakes, last accessed on May 21, 2012.
Rules 161(1) and 162 Communication for EP application No. 13779683.5 dated May 12, 2015.
Russell et al. "Attenuation of skeletal muscle atrophy in cancer cachexia by D-myo-inositol 1,2,6-triphosphate," Cancer Chemother Pharmacol., vol. 64(3), pp. 517-527, Aug. 2009.
Russell, et al., "Mechanism of attenuation by beta-hydroxy-beta-methylbutyrate of muscle protein degradation induced by lipopolysaccharide," Mol Cell Biochem., vol. 330(1-2), pp. 171-179, Oct. 2009.
Russell et al. "Mechanism of attenuation of protein loss in murine C2C12 myotubes by D-myo-inositol 1,2,6-triphosphate," Experimental Cell Research, vol. 316(2), pp. 286-295, Jan. 15, 2010.
Shpigelman et al., "Thermally-induced protein-polyphenol co-assemblies: beta lactoglobulin-based nanocomplexes as protective nanovehicles for EGCG," Food Hydrocolloids, Elsevier BV, NL vol. 24, No. 8 Nov. 1, 2010 pp. 735-743.
Siren & Siren, "Systemic zinc redistribution and dyshomeostasis in cancer cachexia," Journal of Cachexia, Sarcopenia Muscle, vol. 1(1), pp. 123-133, Sep. 2010.
"Sunphenon Epigallocateching-Gallate (EGCg) in Duchenne Muscular Dystrophy (SUNIMUD)" clinicaltrials.gov, Aug. 17, 2010 https://clinicaltricals.gov/ct2/show/study/NCt01183767.
Wang, et al. "Insulin resistance accelerates muscle protein degradation: Activation of the ubiquitin-proteasome pathway by defects in muscle cell signaling," Endocrinology, vol. 147(9), pp. 4160-4168, Sep. 2006.
Westin et al. "Circulating levels of selenium and zinc in relation to nutritional status in patients with head and neck cancer," Arch Otolaryngol Head Neck Surg., vol. 115(9); pp. 1079-1082, Sep. 1989.
Yayabe, Fumihisa, "Industrial application of tea abstracts," www.o-cha.net/english/conferenc2/pdf/2001/ffies/PROC/III-080.pdf retrieved Dec. 12, 2013.
Zhou, et al. "Evidence for adipose-muscle cross talk: opposing regulation of muscle proteolysis by adiponectin and Fatty acids," Endocrinology, vol. 148(12), pp. 5696-5705, Dec. 2007.
English translation of First Office Action in CN Application No. 201380051027.7 dated Mar. 2, 2016.
Examination Review Report for SG Application No. 11201502649W dated Jan. 12, 2016.
Office Action in EP13776697.8, dated Apr. 7, 2016.
Third Party Observations filed in EP13779683.8, dated Jan. 11, 2016.
Hajime Suzuki, "Zinc as an appetite stimulator—The possible role of zinc in the progression of diseases such as cachexia and sarcopenia", Recent patents on food, nutrition & agriculture, 2011, vol. 3, Issue 3, pp. 226-231.
David Scott et al., "Associations between dietary nutrient intake and muscle mass and strength in community dwelling older adults: The Tasmanian older adult cohort study", The American Geriatric Society, 201 0, vol. 58, Issue 11, pp. 2129-2134.
Berrin Bozan et al., "Study of polyphenol content in the seeds of red grape (*Vitis vinifera* L.) varieties cultivated in Turkey and their antiradical activity" Food Chemistry 2008, vol. 109, Issue 2, pp. 426-430.

* cited by examiner

METHODS FOR ENHANCING THE EFFECT OF EGCG ON MITIGATING SKELETAL MUSCLE LOSS

CROSS REFERENCE TO RELATED APPLICATIONS

This application is the U.S. national stage entry of PCT/US2013/063519, with an international filing date of Oct. 4, 2013, which is hereby incorporated by reference herein in its entirety and which claims priority to and any benefit of U.S. Provisional Application No. 61/709,682, filed Oct. 4, 2012, the entire contents of which are incorporated by reference in its entirety.

FIELD OF THE DISCLOSURE

The present disclosure relates to methods for enhancing the efficacy of epigallocatechin gallate ("EGCg") in mitigating skeletal muscle loss in a subject. Particularly, the present disclosure relates to the use of nutritional compositions comprising at least one source of protein, at least one source of EGCg, and at least one source of zinc to a subject to enhance the mitigating effect of EGCg on skeletal muscle loss.

BACKGROUND

Skeletal muscle loss in a subject due to age-, inactivity-, or disease-related disorders may have a negative impact on the overall health and well being of the subject. For example, skeletal muscle loss may lead to weakness, frailty, further muscle loss, susceptibility to injury, a decrease in the ability or desire to exercise, and so forth in the subject. Typically, skeletal muscle loss is regulated by two separate pathways: (1) decreased muscle protein synthesis and (2) increased muscle protein degradation. Together, these pathways generally accelerate and promote rapid muscle loss. Individually, each pathway on its own promotes skeletal muscle loss. Thus, inhibiting or preventing each pathway, individually or together, will have a mitigating effect on skeletal muscle loss.

With respect to the second pathway, age disorders (as evidenced by sarcopenia), disease disorders (as evidenced by cachexia), or general inactivity disorders (e.g., muscle wasting or atrophy due to lack of use or immobilization) may increase or upregulate muscle protein degradation. Thus, the loss of skeletal muscle attributable to age, inactivity, or disease may be mitigated by inhibiting, i.e., decreasing or preventing, muscle protein degradation.

SUMMARY

Disclosed herein are methods for enhancing the efficacy of epigallocatechin gallate ("EGCg") in mitigating skeletal muscle loss in a subject. Providing EGCg to a subject in a nutritional composition reduces muscle protein degradation, thereby mitigating skeletal muscle loss in the subject. The combination of EGCg with zinc in a nutritional composition enhances the mitigating effect that EGCg has on muscle loss. Specifically, a nutritional composition containing both EGCg and zinc requires less EGCg to obtain the same mitigating effect that occurs in a similar nutritional composition containing EGCg but no zinc.

In a first embodiment, a method for enhancing the efficacy of EGCg in mitigating skeletal muscle loss in a subject in need thereof is disclosed. This method includes providing to the subject in need thereof at least one serving per day of a nutritional composition. The nutritional composition comprises at least one source of EGCg in an amount sufficient to provide 10-1000 milligrams (mg) of EGCg per serving; at least one source of zinc in an amount sufficient to provide 2.5-30 mg of zinc per serving; and at least one source of protein in an amount sufficient to provide 5-50 grams (g) of protein per serving. The consumption of at least one serving per day of the nutritional composition results in decreased skeletal muscle loss in the subject as compared to the consumption of a comparative composition containing no zinc.

The first embodiment also provides a nutritional composition for use in mitigating skeletal muscle loss, the nutritional composition comprising at least one source of EGCg in an amount sufficient to provide 10-1000 mg of EGCg per serving, at least one source of zinc in an amount sufficient to provide 2.5-30 mg of zinc per serving, and at least one source of protein in an amount sufficient to provide 5-50 g of protein per serving; the dosage is at least one serving per day. The consumption of at least one serving per day of the nutritional composition results in decreased skeletal muscle loss in a subject as compared to the consumption of a comparative composition containing no zinc.

In addition, the first embodiment provides use of EGCg for the manufacture of a medicament for mitigating skeletal muscle loss, wherein the medicament comprises at least one source of EGCg in an amount sufficient to provide 10-1000 mg of EGCg per serving, at least one source of zinc in an amount sufficient to provide 2.5-30 mg of zinc per serving, and at least one source of protein in an amount sufficient to provide 5-50 g of protein per serving; the dosage is at least one serving per day. The consumption of at least one serving per day of the nutritional composition results in decreased skeletal muscle loss in a subject as compared to the consumption of a comparative composition containing no zinc.

In a second embodiment, a method for reducing the amount of EGCg needed to mitigate skeletal muscle loss attributable to aging, inactivity, or disease in a subject is disclosed. The method includes providing a serving of a liquid nutritional composition to a subject at least once a day. The nutritional composition comprises the following ingredients based on a 150 milliliters (mL) to 500 mL serving size: at least one green tea extract in an amount sufficient to provide 10-1000 mg of EGCg per serving; at least one source of zinc in an amount sufficient to provide 2.5-30 mg of zinc per serving; and at least one source of protein in an amount sufficient to provide 5-50 g of protein per serving. The consumption of the nutritional composition results in less skeletal muscle loss in the subject as compared to the consumption of a comparative composition containing no zinc.

The second embodiment also provides a liquid nutritional composition for use in mitigating skeletal muscle loss attributable to aging, inactivity, or disease, the nutritional composition comprising: at least one green tea extract in an amount sufficient to provide 10-1000 mg of EGCg per serving, at least one source of zinc in an amount sufficient to provide 2.5-30 mg of zinc per serving, and at least one source of protein in an amount sufficient to provide 5-50 g of protein per serving, wherein a serving is from 150 ml to 500 ml and the dosage is at least one serving per day. The consumption of the nutritional composition results in less skeletal muscle loss in the subject as compared to the consumption of a comparative composition containing no zinc.

The second embodiment also provides use of EGCg for the manufacture of a medicament for mitigating skeletal muscle loss attributable to aging, inactivity, or disease wherein the medicament comprises: at least one green tea extract in an amount sufficient to provide 10-1000 mg of EGCg per serving, at least one source of zinc in an amount sufficient to provide 2.5-30 mg of zinc per serving, and at least one source of protein in an amount sufficient to provide 5-50 g of protein per serving, wherein a serving is from 150 ml to 500 ml and the dosage is at least one serving per day. The consumption of the nutritional composition results in less skeletal muscle loss in the subject as compared to the consumption of a comparative composition containing no zinc.

In a third embodiment, a method for reducing the amount of EGCg used to preserve skeletal muscle function in a subject susceptible to loss of skeletal muscle function due to age, inactivity, or disease is disclosed. The method includes providing to the subject a nutritional composition containing a combination of 10-1000 mg of EGCg and 2.5-30 mg of zinc. The consumption of the nutritional composition requires less EGCg to sustain or improve skeletal muscle function as compared to the consumption of a comparative composition containing no zinc.

The third embodiment also provides a nutritional composition for use in preserving skeletal muscle function in a subject susceptible to loss of skeletal muscle function due to age, inactivity, or disease, the nutritional composition comprising: a combination of 10-1000 mg of EGCg and 2.5-30 mg of zinc. The consumption of the nutritional composition requires less EGCg to sustain or improve skeletal muscle function as compared to the consumption of a comparative composition containing no zinc.

The third embodiment also provides use of ECGg for the manufacture of a medicament for preserving skeletal muscle function in a subject susceptible to loss of skeletal muscle function due to age, inactivity, or disease, wherein the medicament comprises a combination of 10-1000 mg of EGCg and 2.5-30 mg of zinc. The consumption of the nutritional composition requires less EGCg to sustain or improve skeletal muscle function as compared to the consumption of a comparative composition containing no zinc.

In a fourth embodiment, a method for reducing the amount of EGCg required to decrease skeletal muscle loss due to aging, inactivity, or disease in a subject in need thereof is disclosed. The method includes providing to the subject in need thereof at least one serving per day of a nutritional composition. The nutritional composition comprises at least one source of EGCg in an amount sufficient to provide 10-1000 mg of EGCg per serving; at least one source of zinc in an amount sufficient to provide 2.5-30 mg of zinc per serving; and at least one source of protein in an amount sufficient to provide 5-50 g of protein per serving. The consumption of at least one serving per day of the nutritional composition results in decreased skeletal muscle loss in the subject as compared to the consumption of a comparative composition containing no zinc.

The fourth embodiment also provides a nutritional composition for use in decreasing skeletal muscle loss due to aging, inactivity, or disease, the nutritional composition comprising at least one source of EGCg in an amount sufficient to provide 10-1000 mg of EGCg per serving, at least one source of zinc in an amount sufficient to provide 2.5-30 mg of zinc per serving, and at least one source of protein in an amount sufficient to provide 5-50 g of protein per serving; the dosage is at least one serving per day. The consumption of at least one serving per day of the nutritional composition results in decreased skeletal muscle loss in a subject as compared to the consumption of a comparative composition containing no zinc.

In addition, the fourth embodiment provides use of EGCg for the manufacture of a medicament for decreasing skeletal muscle loss due to aging, inactivity, or disease, wherein the medicament comprises at least one source of EGCg in an amount sufficient to provide 10-1000 mg of EGCg per serving, at least one source of zinc in an amount sufficient to provide 2.5-30 mg of zinc per serving, and at least one source of protein in an amount sufficient to provide 5-50 g of protein per serving; the dosage is at least one serving per day. The consumption of at least one serving per day of the nutritional composition results in decreased skeletal muscle loss in a subject as compared to the consumption of a comparative composition containing no zinc.

DETAILED DESCRIPTION

The term "muscle loss," unless otherwise indicated herein, refers to the loss of muscle mass, e.g., "skeletal muscle loss" refers to the loss of skeletal muscle mass.

The term "serving," unless otherwise indicated herein, generally refers to an amount of nutritional composition that is consumed in one sitting, which may last up to one or up to two hours.

The term "subject," unless otherwise indicated herein, refers to mammals, including but not limited to, humans. Furthermore, unless otherwise indicated, the term "subject in need thereof" refers to a mammal, including but not limited to, a human exhibiting muscle loss due at least in part to age, inactivity, disease, or combinations thereof. In certain embodiments, the term "subject in need thereof" refers to a mammal, including but not limited to, a human exhibiting muscle loss due at least in part to age. In certain embodiments, the term "subject in need thereof" refers to a mammal, including but not limited to, a human exhibiting muscle loss due at least in part to inactivity. In certain embodiments, the term "subject in need thereof" refers to a mammal, including but not limited to, a human exhibiting muscle loss due at least in part to disease. In certain embodiments, the muscle loss in the subject in need thereof is at least partially attributable to muscle protein degradation.

The term "administering," unless otherwise indicated herein, should be understood to include providing the nutritional product to a subject, the act of consuming the nutritional product, and combinations thereof.

Disclosed herein are methods for enhancing the mitigating, e.g., decreasing or alleviating, effect of EGCg on skeletal muscle loss in a subject. Providing EGCg to a subject in a nutritional composition reduces muscle protein degradation, thereby preventing or at least inhibiting muscle protein degradation, which as discussed herein, promotes skeletal muscle loss. In other words, providing EGCg to a subject in a nutritional composition has a mitigating, e.g., decreasing or alleviating, effect on muscle loss in a subject. Also disclosed herein are methods for reducing the amount of EGCg needed to mitigate skeletal muscle loss attributable to aging, inactivity, disease, or combinations thereof in a subject.

The combination of EGCg with zinc in the nutritional compositions according to the methods disclosed herein enhances the mitigating effect that EGCg has on muscle loss because this combination of EGCg and zinc provides a greater reduction in protein muscle degradation in the subject as compared to EGCg alone. Specifically, when used in combination, EGCg and zinc require less EGCg to obtain the same mitigating effect that occurs in a comparative composition containing no zinc. As used herein, "comparative composition" refers to a similar nutritional composition containing EGCg but no zinc. Unless otherwise indicated, "no zinc" refers to less than 0.00005% by weight of zinc based on the total weight of the composition, or zero zinc, present in the composition. The enhanced effect of using EGCg and zinc in accordance with the methods disclosed herein results in using up to 50% by weight less EGCg when used in combination with zinc as compared to the use of EGCg alone as measured by the amount of EGCg required to obtain the effect, i.e., in other words, up to 50% by weight less EGCg may be used when used in combination with zinc as compared to the comparative composition containing no zinc. In certain embodiments, the enhanced effect of using EGCg and zinc in accordance with the methods disclosed herein results in using up to 60% by weight less EGCg as compared to the comparative composition containing no zinc. In certain other embodiments, the enhanced effect of using EGCg and zinc in accordance with the methods disclosed herein results in using up to 75% by weight less EGCg as compared to the comparative composition containing no zinc.

This enhanced effect resulting from the combination of EGCg and zinc is both surprising and unexpected because zinc, when provided or administered alone (i.e., without EGCg) induces or promotes muscle loss by increasing muscle protein degradation, preventing muscle protein synthesis, or combinations of both. Accordingly, the combination of EGCg and zinc in accordance with the methods disclosed herein provides a surprising and unexpected synergistic enhancement to EGCg's mitigating effect on muscle loss. Thus, the methods utilizing the nutritional compositions containing the combination of EGCg and zinc as disclosed herein will improve the overall muscle health of subjects. These methods may be particularly beneficial for subjects who suffer from skeletal muscle loss due to aging, inactivity, disease, or combinations thereof, including those who are older adults and those who may suffer from chronic muscle dysfunction, muscle atrophy or wasting, as well as those subjects with sarcopenia, cachexia, or other muscle wasting conditions.

Other conditions in a subject that are attributable to muscle protein degradation, including decreased skeletal muscle strength and decreased skeletal muscle quality, may be mitigated by providing EGCg to the subject. It should be understood that the result of muscle protein degradation in a subject is not limited to skeletal muscle loss (i.e., loss of skeletal muscle mass). Muscle protein degradation may also separately affect the skeletal muscle strength of the subject, the skeletal muscle quality of the subject, or both. Specifically, muscle protein degradation may decrease skeletal muscle strength in the subject, and muscle protein degradation may also separately decrease skeletal muscle quality in the subject. Unless otherwise indicated, the term "muscle strength" refers to the amount of force a muscle, or muscle groups in sum, can exert either in acute tests of maximum force, or in time-dependent tests of muscle endurance, time dependent tests of muscle fatigue, or time dependent tests of muscle endurance and fatigue. Additionally, unless otherwise indicated, the term "muscle quality" herein refers to the amount of muscle strength (e.g., in units of force of angular velocity) per unit volume, cross-sectional area, or mass of the corresponding muscle, muscle groups, or arm or leg compartment, i.e., the term "muscle quality" refers to muscle strength per corresponding muscle volume, muscle strength per corresponding muscle cross-sectional area, or muscle strength per corresponding muscle mass. For example, leg muscle quality refers to leg muscle strength/leg muscle volume or leg muscle strength/leg muscle mass. Thus, providing only EGCg to a subject also respectively has a mitigating effect on the decrease in skeletal muscle strength, on the decrease in skeletal muscle quality attributable to muscle protein degradation in the subject, or both. Because the combination of EGCg and zinc provides a greater reduction in protein muscle degradation in the subject as compared to EGCg alone, the combination of EGCg and zinc as disclosed herein also provides a surprising and unexpected synergistic enhancement to EGCg's respective mitigating effects on skeletal muscle strength, skeletal muscle quality, and both skeletal muscle strength and skeletal muscle quality in the subject. In other words, the combination of EGCg and zinc as disclosed herein allows for the use of less EGCg while still obtaining the beneficial muscle result as compared to providing EGCg alone.

Unless otherwise indicated, the term "skeletal muscle function" refers to at least one of skeletal muscle mass, skeletal muscle strength, and skeletal muscle quality. In accordance with certain embodiments disclosed herein, providing nutritional compositions containing a combination of EGCg and zinc to a subject that is susceptible to loss of muscle function due to inactivity, aging, or disease result in sustained or improved muscle function via the reduction of muscle protein degradation in the subject.

In a first embodiment, a method for enhancing the efficacy of EGCg in mitigating skeletal muscle loss in a subject in need thereof is disclosed. This method includes providing to the subject in need thereof at least one serving per day of a nutritional composition. The nutritional composition comprises at least one source of EGCg in an amount sufficient to provide 10-1000 mg of EGCg per serving; at least one source of zinc in an amount sufficient to provide 2.5-30 mg of zinc per serving; and at least one source of protein in an amount sufficient to provide 5-50 g of protein per serving. The consumption of at least one serving per day of the nutritional composition results in decreased skeletal muscle loss in the subject as compared to the consumption of a comparative composition containing no zinc. In accordance with this embodiment, the method further includes administering to the subject in need thereof the at least one serving per day of the nutritional composition.

In a second embodiment, a method for reducing the amount of EGCg needed to mitigate muscle loss attributable to aging, inactivity, or disease in a subject is disclosed. In accordance with certain embodiments of the second embodiment, a method for reducing the amount of EGCg needed to mitigate muscle loss attributable to aging is disclosed. In accordance with certain other embodiments of the second embodiment, a method for reducing the amount of EGCg needed to mitigate muscle loss attributable to inactivity is disclosed. In accordance with yet certain other embodiments of the second embodiment, a method for reducing the amount of EGCg needed to mitigate muscle loss attributable to disease is disclosed. The method according to the second embodiment includes providing a serving of a liquid nutritional composition to a subject at least once a day. The nutritional composition comprises the following ingredients based on a 150 mL to 500 mL serving size: at least one green tea extract in an amount sufficient to provide 10-1000 mg of EGCg per serving; at least one source of zinc in an amount sufficient to provide 2.5-30 mg of zinc per serving; and at least one source of protein in an amount sufficient to provide 5-50 g of protein per serving. The consumption of the nutritional composition results in less skeletal muscle loss in the subject as compared to the consumption of a comparative composition containing no zinc. In accordance with this embodiment, the method further includes administering the serving of the liquid nutritional composition to the subject at least once a day.

In a third embodiment, a method for reducing the amount of EGCg used to preserve skeletal muscle function in a subject susceptible to loss of skeletal muscle function due to age, inactivity, or disease is disclosed. In accordance with certain embodiments of the third embodiment, a method for reducing the amount of EGCg used to preserve skeletal muscle function in a subject susceptible to loss of skeletal muscle function due to age is disclosed. In accordance with certain other embodiments of the third embodiment, a method for reducing the amount of EGCg used to preserve skeletal muscle function in a subject susceptible to loss of skeletal muscle function due to inactivity is disclosed. In accordance with yet certain other embodiments of the third embodiment, a method for reducing the amount of EGCg used to preserve skeletal muscle function in a subject susceptible to loss of skeletal muscle function due to disease is disclosed. The method according to the third embodiment includes providing to the subject a nutritional composition containing a combination of 10-1000 mg of EGCg and 2.5-30 mg of zinc. The consumption of the nutritional composition requires less EGCg to sustain or improve skeletal muscle function as compared to the consumption of a comparative composition containing no zinc. In other words, the combination of EGCg and zinc reduces the amount of EGCg needed to sustain or improve skeletal muscle function as compared to a comparative composition containing no zinc. In accordance with this embodiment, the method further includes administering to the subject the nutritional composition. Moreover, in accordance with this embodiment, the nutritional composition may further comprise at least one source of protein in an amount sufficient to provide 5-50 g of protein per serving.

In a fourth embodiment, a method for reducing the amount of EGCg required to decrease skeletal muscle loss due to aging, inactivity, or disease in a subject in need thereof is disclosed. In accordance with certain embodiments of the fourth embodiment, a method for reducing the amount of EGCg required to decrease skeletal muscle loss due to aging is disclosed. In accordance with certain other embodiments of the fourth embodiment, a method for reducing the amount of EGCg required to decrease skeletal muscle loss due to inactivity is disclosed. In accordance with yet certain other embodiments of the fourth embodiment, a method for reducing the amount of EGCg required to decrease skeletal muscle loss due to disease is disclosed. The method according to the fourth embodiment includes providing to the subject in need thereof at least one serving per day of a nutritional composition. The nutritional composition comprises at least one source of EGCg in an amount sufficient to provide 10-1000 mg of EGCg per serving; at least one source of zinc in an amount sufficient to provide 2.5-30 mg of zinc per serving; and at least one source of protein in an amount sufficient to provide 5-50 g of protein per serving. The consumption of at least one serving per day of the nutritional composition results in decreased skeletal muscle loss in the subject as compared to the consumption of a comparative composition containing no zinc. In accordance with this embodiment, the method further includes administering to the subject in need thereof at least one serving per day of the nutritional composition.

In accordance with the first, second, third, and fourth embodiments disclosed herein, the nutritional compositions disclosed herein are useful to provide supplemental, primary, or sole sources of nutrition, including providing the subjects one or more benefits as described herein. In accordance with certain methods of the first, second, third, and fourth embodiments, the nutritional compositions are provided as needed to supply the desired level of nutrition, including providing at least one serving per day. The foregoing should be understood to include, but not be limited to, one serving per day, two servings per day, three servings per day, and four servings per day. Typically the nutritional compositions are provided in at least one serving per day or at least two servings per day.

In certain of the first, second, third, and fourth embodiments, the nutritional compositions are formulated for consumption in any known or otherwise suitable oral, liquid nutritional product form. Thus, in the methods of the first, second, third, and fourth embodiments, the step of administering includes the oral consumption of the nutritional composition by the subject, and in certain embodiments, the step of administering includes the oral consumption of the nutritional composition as a liquid nutritional product by the subject.

Any liquid nutritional or semi-liquid nutritional product form, including combinations or variations thereof, are suitable for use herein, provided that such forms allow for safe and effective oral consumption by the subject of the ingredients as also defined herein. The term "liquid nutritional product" as used herein, unless otherwise specified, includes nutritional compositions in ready-to-drink liquid form, concentrated liquid form, or a reconstitutable powder form. The term "reconstitutable powder" unless otherwise indicated herein, refers to a powdered form of the nutritional composition that requires the addition of liquid, e.g., water, to be reconstituted into a liquid form for consumption. The liquid nutritional product may be formulated as a suspension, an emulsion, a solution, and the like. The term "semi-liquid nutritional product," as used herein, unless otherwise specified, refers to nutritional compositions that are intermediate in properties, such as flow properties, between liquids and solids. Non-limiting examples of semi-liquids include shakes, yogurts, pudding, and gels.

Non-limiting examples of liquid nutritional products include snack and meal replacement liquid products, hot or cold beverages, carbonated or non-carbonated beverages, juices or other acidified beverages, fermented beverages, milk- or soy-based beverages, shakes, coffees, teas, enteral feeding compositions, and so forth.

In accordance with the first, second, third, and fourth embodiments disclosed herein, when the nutritional composition is a liquid nutritional product, the primary constituent of the liquid phase of the product is water. These nutritional compositions contain up to about 95% of water by weight of the nutritional composition, including from 50% to 95%, also including from 60% to 90%, and also including from 70% to 85%, of water by weight of the nutritional composition.

In accordance with the first, second, third, and fourth embodiments disclosed herein, when the nutritional composition is a liquid nutritional product, the nutritional compositions in their final, consumable form generally contain an amount of water sufficient to provide a serving ranging from about 100 mL to about 600 mL, including about 150 mL to about 500 mL, including from about 175 mL to about 475 mL, and including from about 225 mL to about 375 mL. In certain of the preceding embodiments, when the nutritional compositions is a reconstitutable powder, the final, consumable form is the reconstituted form containing both the powder and the liquid phase.

In accordance with the first, second, third, and fourth embodiments, the nutritional compositions disclosed herein contain at least one source of EGCg in an amount sufficient to provide 10-1000 mg of EGCg per serving and at least one source of zinc in an amount sufficient to provide 2.5-30 mg of zinc per serving. Typically, in accordance with the first, second, third, and fourth embodiments, the total amount of EGCg provided to the subject, divided amongst all servings, does not exceed 1000 mg EGCg per day. For example, if two identical servings of the nutritional composition are provided in one day, the total amount of EGCg contained in each serving does not exceed 500 mg EGCg.

As previously mentioned, according to the first, second, third, and fourth embodiments described herein, the nutritional composition comprises at least one source of EGCg in an amount sufficient to provide 10-1000 mg of EGCg per serving, including 125-750 mg of EGCg per serving, including 125-500 mg of EGCg per serving, including 250-500 mg of EGCg per serving, including 60-375 mg of EGCg per serving, and including 125-250 mg of EGCg per serving.

In certain of the preceding embodiments, when one serving of the nutritional composition is provided per day, the nutritional composition comprises at least one source of EGCg in an amount sufficient to provide up to 1000 mg of EGCg, including 125-750 mg of EGCg, and including 250-500 mg of EGCg. In certain other embodiments, when two servings of the nutritional composition are provided per day, the nutritional composition comprises at least one source of EGCg in an amount sufficient to provide up to 500 mg of EGCg, including 60-375 mg of EGCg, and including 125-250 mg of EGCg.

As previously discussed, according to the first, second, third, and fourth embodiments described herein, the nutritional composition contains at least one source of EGCg in an amount sufficient to provide 10-1000 mg of EGCg per serving. EGCg is a polyphenol, specifically a catechin, that is desirable for many therapeutic and nutritional benefits, including mitigating muscle loss or preserving muscle function in a subject. EGCg generally is the most abundant polyphenol present in green tea. Accordingly, suitable sources of EGCg for the nutritional compositions disclosed herein are green tea-based sources including, but not limited to, green tea extracts in which EGCg alone, or in combination with other polyphenol compounds, are isolated from green tea as an extract. Examples of such suitable green tea extracts are in the form of a liquid with a high concentration of the polyphenols, a solid (e.g., a powder), and mixtures thereof. In certain embodiments where green tea extract is utilized, the extract is decaffeinated such that it contains less than 1% by weight caffeine, or even less than 0.5% by weight caffeine. In addition to containing EGCg, suitable green tea extracts used with the nutritional compositions disclosed herein may contain other polyphenols including other catechins such as catechin (i.e., (+)-catechin, also known as "C"), epicatechin ("EC"), gallocatechin ("GC"), epigallocatechin ("EGC"), and epicatechin gallate ("ECg"); flavones such as apigenin, isoviloxin, sapotarin, and vicenin-2; flavonols such as kaempherol, quercetin, myricetin; condensed flavanoids, and tannin glycosides. Accordingly, in certain embodiments, in addition to EGCg, the at least one source of EGCg further comprises at least one of C, EC, GC, EGC, ECg, and combinations thereof. In certain embodiments, sources of EGCg other than green tea-based sources may be utilized. These sources include, but are not limited to, oolong tea-based sources such as oolong tea, oolong tea extracts, and the like; white tea-based sources such as white tea, white tea extracts, and the like; macha tea, macha tea extracts, and the like; yellow tea, yellow tea extracts, and the like; and dark tea (i.e., Chinese dark tea), dark tea extracts, and the like.

In certain embodiments, the at least one source of EGCg contains at least 30% by weight solids of EGCg. In accordance with certain of the preceding embodiments, the at least one source of EGCg contains at least 45% by weight solids of EGCg. In one embodiment, the at least one source of EGCg contains 30-100% by weight solids of EGCg. In certain embodiments, the at least one source of EGCg contains 45-100% by weight solids of EGCg. Furthermore, in certain embodiments, the at least one source of EGCg contains 90-100% by weight solids of EGCg.

As mentioned above, when EGCg and zinc are used in combination, a nutritional composition disclosed herein requires less EGCg to obtain the same mitigating effects that occur in a comparative composition containing EGCg but no zinc. The need for less EGCg translates to the need for less of the at least one source of EGCg as well. Accordingly, less of the at least one source of EGCg, e.g., less of the green tea extract, is needed when used in combination with zinc to obtain the same effects in the subject provided by a comparative composition containing EGCg but no zinc.

As previously discussed, according to the first, second, third, and fourth embodiments described herein, the nutritional composition contains at least one source of zinc in an amount sufficient to provide 2.5-30 mg of zinc per serving. In accordance with the first, second, third, and fourth embodiments disclosed herein, a serving of the nutritional composition contains a molar ratio of 0.017:1 to 4.3:1 zinc to EGCg. In certain of the preceding embodiments, a serving of the nutritional composition contains a molar ratio of 0.05:1 to 3:1 zinc to EGCg. In certain of the preceding embodiments, a serving of the nutritional composition contains a molar ratio of 0.1:1 to 2:1 zinc to EGCg.

Non-limiting examples of sources of zinc for the nutritional compositions disclosed herein include zinc salts such as zinc sulfate, zinc gluconate, zinc iodide, zinc chloride, zinc citrate, zinc carbonate, zinc hydroxide, zinc lactate, zinc acetate, zinc fluoride, zinc bromide, zinc sulfonate, zinc glucuronate, and combinations thereof.

As previously mentioned, according to the first, second, third, and fourth embodiments described herein, the nutritional composition comprises at least one source of zinc in an amount sufficient to provide 2.5-30 mg of zinc per serving, including 5-20 mg of zinc per serving, and including 7.5-18 mg of zinc per serving.

In accordance with certain of the first, second, third, and fourth embodiments, the nutritional compositions disclosed herein include at least one source of protein in an amount sufficient to provide 5-50 g of protein per serving. In accordance with certain of the preceding embodiments, the nutritional composition may comprise 6-45 g of protein per serving. In other embodiments according to the first, second, third, and fourth embodiments, the nutritional composition may comprise 10-30 g of protein per serving. Virtually any source of protein may be used so long as it is suitable for nutritional compositions and is otherwise compatible with any other selected ingredients or features in the nutritional composition. For example, the at least one source of protein may include, but is not limited to, intact, hydrolyzed, and partially hydrolyzed protein, which may be derived from any known or otherwise suitable source such as milk (e.g., casein, whey), animal (e.g., meat, fish), cereal (e.g., rice, corn), vegetable (e.g., soy, pea), and combinations thereof. The at least one source of protein may also include a mixture amino acids (often described as free amino acids) known for use in nutritional products, including the amino acids described herein, or a combination of such amino acids with the intact, hydrolyzed, and partially hydrolyzed proteins described herein. The amino acids may be naturally occurring or synthetic amino acids.

More particular examples of suitable sources of protein used in the nutritional compositions disclosed herein include, but are not limited to, whey protein concentrates, whey protein isolates, whey protein hydrolysates, acid caseins, sodium caseinates, calcium caseinates, potassium caseinates, casein hydrolysates, milk protein concentrates, milk protein isolates, milk protein hydrolysates, nonfat dry milk, condensed skim milk, soy protein concentrates, soy protein isolates, soy protein hydrolysates, pea protein concentrates, pea protein isolates, pea protein hydrolysates, collagen proteins, and the like. The at least one source of protein can include any individual protein or combination of the various sources of protein listed above.

In certain of the first, second, third, and fourth embodiments when the nutritional composition has a pH ranging from 2 to 5, the at least one source of protein is limited to proteins that are soluble in an aqueous composition at this pH level. Examples of such proteins soluble in an aqueous composition at a pH of 2 to 5, include, but are not limited to, sources of whey-based proteins such as whey protein concentrates, whey protein isolates including either acidified or non-acidified whey protein isolates, whey protein hydrolysates; certain soy-based proteins such as acidified soy protein isolates and soy protein hydrolysates; certain casein-based proteins such as casein hydrolysates; certain pea-based proteins such as pea hydrolysates; and the like.

In certain embodiments according to the first, second, third, and fourth embodiments, the nutritional compositions may also include an ingredient selected from the group consisting of at least one source of carbohydrates, at least one source of fat, and combinations thereof.

In certain of the first, second, third, and fourth embodiments in which the nutritional composition contains carbohydrates, the nutritional composition may comprise 15-110 g of at least one source of carbohydrate per serving. In other embodiments according to the first, second, third, and fourth embodiments, the nutritional composition may comprise 25-90 g of at least one source of carbohydrate per serving. In yet other embodiments according to the first, second, third, and fourth embodiments, the nutritional composition may comprise 40-65 g of at least one source of carbohydrate per serving.

The at least one source of carbohydrate suitable for use in the nutritional compositions disclosed herein may be simple, complex, or variations or combinations thereof. Generally, any source of carbohydrate may be used so long as it is suitable for use in nutritional compositions and is otherwise compatible with any other selected ingredients or features present in the nutritional composition. Non-limiting examples of a source of carbohydrate suitable for use in the nutritional emulsions described herein may include maltodextrin, hydrolyzed or modified starch or cornstarch; glucose polymers; corn syrup; corn syrup solids; rice-derived carbohydrates; sucrose; glucose; fructose; lactose; high fructose corn syrup; honey; sugar alcohols (e.g., maltitol, erythritol, sorbitol); sources of soluble fibers such as resistant starches, gum arabic, pectins, beta-glucans, and the like; and combinations thereof.

As mentioned above, in certain of the first, second, third, and fourth embodiments, the nutritional composition may include at least one source of fat. In certain of the embodiments containing fat, the nutritional composition may comprise 2-45 g of at least one source of fat per serving. In other embodiments according to the first, second, third, and fourth embodiments, the nutritional composition may comprise 5-35 g of at least one source of fat per serving. In yet other embodiments according to the first, second, third, and fourth embodiments, the nutritional composition may comprise 10-30 g of at least one source of fat per serving. In the embodiments of the nutritional composition containing at least one source of fat, the nutritional composition is in the form of a liquid emulsion.

In general, any source of fat may be used so long as it is suitable for use in oral nutritional compositions and is otherwise compatible with any other selected ingredients or features present in the nutritional composition. Typically, the nutritional compositions disclosed herein that contain fat are aqueous emulsions having a pH ranging from 5 to 8, including a pH of 6 to 7, and including a pH of 6.6 to 7. As previously mentioned, the source of fat may be derived from plants, animals, and combinations thereof. Non-limiting examples of suitable sources of fat for use in the nutritional compositions described herein include coconut oil, fractionated coconut oil, soy oil, corn oil, olive oil, safflower oil, high oleic safflower oil, MCT oil (medium chain triglycerides), sunflower oil, high oleic sunflower oil, palm and palm kernel oils, palm olein, canola oil, marine oils, cottonseed oils, interesterified oils, transesterified oils, and combinations thereof.

In other embodiments according to the first, second, third, and fourth embodiments, the nutritional composition may contain a limited amount of fat. The limited amount of fat may be due at least in part to the desired clarity and desired pH of the liquid nutritional composition. Typically, the liquid nutritional compositions desired to be clear, or at least substantially translucent, are substantially free of fat. As used herein "substantially free of fat" refers to nutritional compositions containing less than 0.5%, and including less than 0.1% fat by weight of the total composition. "Substantially free of fat" also may refer to nutritional compositions disclosed herein that contain no fat, i.e., zero fat. Furthermore, those liquid nutritional compositions that have a desired acidic pH in the range of 2 to 5, e.g., juices, fruit juices, fruit-flavored beverages, etc., typically are substantially free of fat. Liquid nutritional compositions that are both clear and have a pH ranging from 2 to 5 are also typically substantially free of fat. In certain embodiments according to the first, second, third, and fourth embodiments, the nutritional composition is a clear liquid nutritional product having a pH of 2-5 and having no more than 0.5 weight % fat based on the total weight of the nutritional composition. In certain of the preceding embodiments, the pH of the nutritional composition may be from 2.5 to 4.6, including a pH of 3 to 3.5. In those embodiments of the nutritional compositions that are substantially free of fat but have some amount of fat present, the fat may be present as a result of being inherently present in another ingredient (e.g., a source of protein) or may be present as a result of being added as one of more separate sources of fat.

The amount or concentration of the at least one source of fat, the at least one source of protein, and at least one source of carbohydrate present in certain embodiments according to the first, second, third, and fourth embodiments of the nutritional compositions described herein may vary widely depending on the product formulation of the nutritional composition (e.g., clear liquid, a fat-based emulsion, etc.). In addition, the amount or concentration of the at least one source of fat, the at least one source of protein, and at least one source of carbohydrate present in certain embodiments according to the first, second, third, and fourth embodiments of the nutritional compositions described herein may be characterized based upon a percentage of the total calories per serving in the nutritional composition. For example, in certain embodiments according to the first, second, third, and fourth embodiments, the amount or concentration of the at least one source of fat, the at least one source of protein, and the at least one source of carbohydrate present in the nutritional composition can be within the ranges described in Samples A-C, as shown in the Table 1 below.

TABLE 1

| Nutrient (% total calories) | Sample A | Sample B | Sample C |
| --- | --- | --- | --- |
| Carbohydrate | 0-94 | 20-85 | 35-55 |
| Fat | 0-94 | 5-50 | 15-35 |
| Protein | 6-100 | 10-50 | 20-50 |

In accordance with the first, second, third, and fourth embodiments, the nutritional compositions have a calorie content of 50-500 kilocalorie (kcal) per serving, including 100-450 kcal per serving, and including 150-350 kcal per serving. In certain embodiments, the at least one source of protein present in the nutritional composition provides substantially all of the calories in the composition. In other embodiments in which carbohydrates are present, the at least one source of protein and the at least one source of carbohydrates in combination provide substantially all of the calories in the composition. In other embodiments in which fat is present, the at least one source of protein and the at least one source of fat in combination provide substantially all of the calories in the composition. In yet other embodiments where both fat and carbohydrates are present, the at least one source of protein, the at least one source of fat, and the at least one source of carbohydrates in combination provide substantially all of the calories in the composition. Non-limiting examples of this embodiment, i.e., a nutritional composition containing at least one source of protein, at least one source of fat, and at least one source of carbohydrates, are shown in Table 1 as Samples B and C. The amount of the at least one source of protein and, if present, the relative amount of the at least one source of carbohydrates or the at least one source of fat, can be adjusted to obtain the desired caloric density of the nutritional composition.

In certain embodiments according to the first, second, third, and fourth embodiments, the nutritional compositions disclosed herein may include other compounds or sources of such compounds that are anabolic for muscle, stimulate muscle protein synthesis, decrease muscle protein degradation, or combinations thereof. Examples of such compounds include, but are not limited to, leucine, isoleucine, valine, glycine, histidine, lysine, methionine, phenylalanine, threonine, tryptophan, carnitine, carnosine, creatine, alpha-ketoisocaproate, and metabolites of any of the foregoing. In certain embodiments according to the first, second, third, and fourth embodiments, the nutritional compositions disclosed herein include at least one source of a compound selected from the group consisting of leucine, isoleucine, valine, glycine, histidine, lysine, methionine, phenylalanine, threonine, tryptophan, carnitine, carnosine, creatine, alpha-ketoisocaproate, metabolites of any of the foregoing, and combinations thereof. A non-limiting example of a suitable metabolite of leucine is beta-hydroxy-beta-methylbutyrate (HMB). Suitable sources of HMB include HMB as the free acid, a salt, an anhydrous salt, an ester, a lactone, or other product forms that otherwise provide a bioavailable form of HMB in the nutritional product. Non-limiting examples of suitable salts of HMB for use herein include HMB salts, hydrated or anhydrous, of sodium, potassium, magnesium, chromium, calcium, or other non-toxic salt form. Ca-HMB monohydrate is preferred and is commercially available from Technical Sourcing International (TSI of Salt Lake City, Utah) and from Lonza Group Ltd. (Basel, Switzerland). In certain of the embodiments containing HMB, the nutritional composition may comprise 0.5-2.5 g of HMB per serving, including 1-2 g of HMB per serving.

In certain of the preceding embodiments, the nutritional compositions disclosed herein include at least one source of a branched chain amino acid selected from the group consisting of leucine, isoleucine, valine, and combinations thereof. In accordance with other embodiments according to the first, second, third, and fourth embodiments, the nutritional compositions disclosed herein include at least one source of a compound selected from the group consisting of HMB, beta-alanine, and combinations thereof.

In addition, nutritional compositions disclosed herein may include at least one food-grade acid. As discussed above, certain of the nutritional compositions according to the first, second, third, and fourth embodiments, disclosed herein have a pH of 2 to 5, and in certain of the preceding embodiments, a pH of 2.5 to 4.6 or a pH of 3 to 3.5. The at least one food-grade acid may be added to the nutritional composition to adjust the pH of the overall nutritional composition to obtain a pH from 2 to 5, a pH from 2.5 to 4.6, or a pH from 3 to 3.5. Any suitable food-grade acid that is capable of adjusting the pH of the nutritional composition to a pH ranging from 2.5 to 4.6, a pH ranging from 2.5 to 4, or a pH ranging from 3 to 3.5 may be used. Non-limiting examples of such suitable food-grade acids include citric acid, acetic acid, lactic acid, maleic acid, ascorbic acid, phosphoric acid, hydrochloric acid, and the like. The amount or concentration of the food-grade acid required to obtain the intended pH depends on various factors, such as the initial pH of the finalized formulation, the relative strength or weakness of the selected food-grade acid, the concentration of the selected food-grade acid, the quantity of the nutritional composition, etc. The type of acid selected may also be based on the type of flavor desired in the nutritional composition, e.g., for a lemon flavored product, citric acid is more suitable, while for the apple flavored product, maleic acid is more suitable. In addition, the pH can also be adjusted by addition of clear juices, e.g., cranberry, lemon juice, lime juice, pineapple juice, and the like, including mixtures and combinations thereof, can be added to adjust the pH to desired levels. Furthermore, in the case of the over-addition of acid, a suitable food grade base, e.g., sodium hydroxide, calcium hydroxide, potassium hydroxide and the like, can be used to bring the pH of the nutritional composition to the desired level.

In certain embodiments, the nutritional compositions disclosed herein may include at least one high intensity sweetener to counter, mask, or otherwise obscure the potent taste of the EGCg present, which may be described as sour, astringent, and bitter, as well as to counter, mask, or otherwise obscure the taste any of the other polyphenol in the source of EGCg that may be present, in the nutritional composition. Examples of suitable high intensity sweeteners include, but are not limited to, sucralose, acesulfame potassium (also known as "acesulfame K" or "ace K"), aspartame, stevia, neotame, neohesperidine DC, alitame, monellin, thaumatin, mogrosides, monk fruit, and the like. The at least one high intensity sweetener may include any individual or combination of high intensity sweeteners listed above. The amount of the at least one high intensity sweetener in the nutritional composition may vary depending upon the particular high intensity sweetener selected, other ingredients in the formulation, and other formulation or product target variables. Different high intensity sweeteners themselves have different sweetness intensities (e.g., acesulfame K is approximately 200 times sweeter than sucrose as compared to sucralose which is approximately 600 times sweeter than sucrose), and therefore may require more or less sweetener relative to other sweeteners. Furthermore, certain carbohydrates are sweeteners that may at least partially counter or at least partially mask the taste of the EGCg, and any other polyphenols that may be present, in certain embodiments of the nutritional composition disclosed herein that contain carbohydrates.

In certain embodiments according to the first, second, third, and fourth embodiments disclosed herein, the nutritional composition may comprise a viscosity agent, e.g., thickening agent. Typically, the viscosity agent is used in the thicker types of nutritional compositions, e.g., the fat-based emulsions, shakes, etc. Any viscosity agent that is known or otherwise suitable for use in a nutritional composition is also suitable for use herein, some non-limiting examples of which include starches, such as modified corn starch, wheat starch (including pregelatinized wheat starch), potato starch, rice starch, tapioca starch, and the like; blends of cellulose gel and cellulose gum; blends of microcrystalline cellulose and sodium carboxymethyl cellulose; pectin; carrageenan; agar; gellan gum; alginates; gum *acacia*; gelatin; methyl cellulose; hydroxypropylcellulose; and combinations thereof. In certain embodiments according to the first, second, third, and fourth embodiments disclosed herein, the viscosity agent is present in an amount of 0 to about 5.0%, including from about 0.1% to about 3%, including from about 0.5% to about 1.5%, by weight of the nutritional composition.

In certain of the first, second, third, and fourth embodiments, the nutritional compositions disclosed herein may also contain other ingredients, non-limiting examples of which include, preservatives, antioxidants in addition to the EGCg and other polyphenols that may be present in the at least one source of EGCg, buffers, pharmaceutical actives, additional nutrients, colorants, flavors, emulsifiers, and antifoam agents.

In addition, in certain of the first, second, third, and fourth embodiments, the nutritional compositions disclosed herein may also contain vitamins or related nutrients including, but not limited to, curcumin, lutein, fish oil, vitamin A, vitamin D, vitamin E, vitamin K, thiamine, riboflavin, pyridoxine, vitamin B12, carotenoids, niacin, folic acid, pantothenic acid, biotin, vitamin C, choline, inositol, salts, derivatives thereof, and combinations thereof.

Additionally, in accordance with certain of the first, second, third, and fourth embodiments, the nutritional compositions disclosed herein may also contain minerals, including, but not limited to, phosphorus, magnesium, iron, manganese, copper, sodium, potassium, molybdenum, chromium, selenium, chloride, and combinations thereof.

In certain of the first, second, third, and fourth embodiments, the nutritional compositions disclosed herein may be formulated in a manner so as to have a low glycemic index. In certain nutritional compositions disclosed herein that contain carbohydrates, the relative amount and type of the at least one source of carbohydrates, amongst other ingredients, can be adjusted to obtain the desired glycemic index of the nutritional composition. In certain of the embodiments according to the first, second, third, and fourth embodiment, the nutritional composition has a glycemic index less than or equal to 50. In other embodiments, the nutritional composition has a glycemic index less than or equal to 40, including less than or equal to 30, and including less than or equal to 20.

The various embodiments of the nutritional compositions disclosed herein may also be substantially free of any optional ingredient or feature described herein, provided that the remaining nutritional composition still contains all of the required ingredients or features as described herein. In this context, and unless otherwise specified, the term "substantially free" means that the selected nutritional compositions contain less than a functional amount of the optional ingredient, typically less than 0.5%, including less than 0.1% and also including zero, by weight of such optional ingredient.

Exemplary formulations of liquid nutritional compositions disclosed herein in accordance with the first, second, third, and fourth embodiments, are provided below in Tables 2 and 3. All ingredient amounts listed in Tables 2 and 3 are listed as kilogram per 1000 kg batch of product, unless otherwise indicated. Table 2 shows an exemplary formulation of a emulsion-type liquid nutritional composition containing fat, protein, and carbohydrates and has a pH in the range of 6.6-7. Assuming a density of 1.075 g/mL and a serving size of about 237 mL (about 8 fl. oz.), a nutritional composition made according to the formulation shown in Table 2 has about 177 mg of EGCg per serving and about 14 mg of zinc per serving.

TABLE 2

| INGREDIENTS | Amount (kg/1000 kg) |
|---|---|
| Water | Quantity Sufficient |
| EGCg-containing Green Tea Extract[1] | 1.390 |
| Zinc Sulfate, Monohydrate[2] | 0.11 |
| Sucrose | 89.1 |
| Maltodextrin | 69.1 |
| Milk Protein Concentrate | 38.6 |
| Soy Oil | 13.3 |
| Canola Oil | 5.3 |
| Soy Protein Concentrate | 4.7 |
| Corn Oil | 4.1 |
| Potassium Citrate | 2.7 |
| Natural and artificial Vanilla Flavor | 2.0 |
| Magnesium Phosphate Dibasic | 1.9 |
| Sodium Citrate | 1.6 |
| Soy Lecithin | 1.4 |
| Tricalcium Phosphate | 1.3 |
| Magnesium Chloride | 1.2 |
| Sodium Chloride | 0.718 |
| Choline Chloride | 0.480 |
| Ascorbic Acid | 0.469 |
| Carrageenan | 0.450 |
| Ultra Trace Mineral/Trace Mineral Premix (this premix contains Zinc Sulfate, Monohydrate)[3] | 0.364 |

TABLE 2-continued

| INGREDIENTS | Amount (kg/1000 kg) |
| --- | --- |
| Potassium Hydroxide (Processing aid) | 0.323 |
| Potassium Chloride | 0.308 |
| Vitamin Premix[4] | 0.1465 |
| Potassium Iodide | 0.000207 |

[1] SUNPHENON ® 90D (available from Taiyo International, Inc. of Minneapolis, Minnesota) is a green tea extract that contains approximately 50% by weight of EGCg, i.e., 1.390 kg of green tea extract contains approximately 0.695 kg EGCg.
[2] The zinc sulfate, monohydrate contains about 36.4% by weight of zinc, i.e., 0.11 kg of zinc sulfate monohydrate contains 0.040 kg zinc.
[3] The 0.364 kg of the UT/UTM premix contains 0.0456 kg of zinc sulfate, monohydrate, of which 36.4% by weight is zinc. Thus, the 0.364 kg UT/UTM premix contains 0.017 kg zinc.
[4] Vitamin premix includes one or more of the following: dl-Alpha-Tocopheryl Acetate, Vitamin A Palmitate, Phylloquinone, Vitamin D3, Niacinamide, d-Calcium Pantothenate, Thiamine Chloride Hydrochloride, Pyridoxine Hydrochloride, Riboflavin, Folic Acid, Biotin, Cyanocobalamin, etc.

Table 3 shows an exemplary formulation of a clear-type liquid nutritional composition that is substantially free of fat and having a pH in the range of 3-3.5. Assuming a density of 1.05 g/mL and a serving size of about 296 mL (about 10 fl. oz.), a nutritional composition made according to the formulation shown in Table 3 has about 188 mg of EGCg per serving and about 18 mg of zinc per serving.

TABLE 3

| INGREDIENTS | Amount (kg/1000 kg) |
| --- | --- |
| Water | Quantity Sufficient |
| Sucrose | 50.7 |
| Corn syrup solids | 61.3 |
| Zinc Sulfate, Monohydrate[1] | 0.11 |
| Acidified Whey Protein Isolate | 35.7 |
| Citric Acid | 2.00 |
| Flavoring | 2.00 |
| EGCg-containing Green Tea Extract[2] | 1.212 |
| Ascorbic Acid | 0.535 |
| Liquid Sucralose (25%) | 0.275 |
| Ultra Trace Mineral/Trace Mineral Premix (this premix contains Zinc Sulfate, Monohydrate)[3] | 0.230 |
| Vitamin Premix[4] | 0.219 |
| Acesulfame Potassium | 0.110 |
| Antifoam processing aid (non-silicone) | 0.060 |
| Coloring | 0.0589 |
| Natural and Artificial Peach Flavor | 2.0 |
| Folic Acid | 0.0013 |
| Potassium Iodide | 0.000204 |

[1] The zinc sulfate, monohydrate contains about 36.4% by weight of zinc, i.e., 0.11 kg of zinc sulfate monohydrate contains 0.040 kg zinc.
[2] SUNPHENON ® 90D, which is a green tea extract that contains approximately 50% by weight of EGCg, i.e., 1.212 kg of green tea extract contains approximately 0.606 kg EGCg.
[3] The 0.230 kg of the UT/UTM premix contains 0.0521 kg of zinc sulfate, monohydrate of which 36.4% by weight is zinc. Thus, the 0.230 kg UT/UTM premix contains 0.019 kg zinc.
[4] Vitamin premix includes one or more of the following: dl-Alpha-Tocopheryl Acetate, Vitamin A Palmitate, Phylloquinone, Vitamin D3, Niacinamide, d-Calcium Pantothenate, Thiamine Chloride Hydrochloride, Pyridoxine Hydrochloride, Riboflavin, Folic Acid, Biotin, Cyanocobalamin, etc.

The various embodiments of the nutritional composition according to the first, second, third, and fourth embodiments disclosed herein may be prepared by any process or suitable method (now known or known in the future) for making the selected product form, such a liquid or semi-liquid nutritional composition.

In one suitable manufacturing process for preparing the emulsion-type liquid nutritional compositions (e.g., such as the composition listed in Table 2 above), for example, at least three separate slurries are prepared, including a protein-in-fat (PIF) slurry, a carbohydrate-mineral (CHO-MN) slurry, and a protein-in-water (PIW) slurry. The PIF slurry is formed by heating and mixing an oil (e.g., canola oil, corn oil, etc.) and then adding an emulsifier (e.g., lecithin), fat soluble vitamins, and a portion of the total protein (e.g., milk protein concentrate, etc.) with continued heat and agitation. The CHO-MN slurry is formed by adding with heated agitation to water: minerals (e.g., potassium citrate, dipotassium phosphate, sodium citrate, etc.), including trace and ultra trace minerals (TM/UTM premix), and thickening or viscosity agents (e.g., cellulose gel, gellan, carrageenan). The resulting CHO-MIN slurry is held for 10 minutes with continued heat and agitation before adding additional minerals (e.g., potassium chloride, magnesium carbonate, potassium iodide, etc.) and the carbohydrates (e.g., fructooligosaccharide, sucrose, corn syrup, etc.). The PIW slurry is then formed by mixing with heat and agitation the remaining protein.

In accordance with this process, the three slurries are blended together with heat and agitation and the pH is adjusted to the desired range, e.g., from 6.6 to 7, after which the composition is subjected to high-temperature short-time ("HTST") processing. The composition is heat treated, emulsified, homogenized, and cooled during HTST. Water soluble vitamins and ascorbic acid are added (if applicable), the pH is again adjusted (if necessary), flavors are added and any additional water can be added to adjust the solids content to the desired range. The source of EGCg, e.g., green tea extract, is prepared as a solution (e.g., 1%) by adding to water and agitating for 0-24 hours. Furthermore, the source of zinc, e.g., zinc salt, is then added to the solution containing the EGCg and agitated 0-24 hours. Alternatively, the source of zinc is added to water and is agitated for 0-24 hours, followed by the addition of the source of EGCg and agitation from 0-24 hours. Furthermore, as another alternative, the source of EGCg and the source of zinc are concurrently added to water and agitated 0-24 hours. The solution of EGCg and zinc is added to the composition containing the other ingredients and is agitated for a period of time, e.g., 5-60 minutes, to ensure homogeneous distribution of the EGCg and zinc in the composition. The agitation associated with the preparation of the solution containing EGCg and zinc, along with the addition of the EGCg and zinc solution to the other ingredients, may take place at 4° C. to 50° C. At this point, the liquid nutritional composition may be packaged and sterilized according to any suitable sterilization technique, such as aseptic, retort, or hot-fill sterilization.

In another suitable manufacturing process for preparing the clear-type or more acidic-type form of liquid nutritional compositions (e.g., such as the composition listed in Table 3 above), for example, protein is added to room temperature water in a kettle. The protein and water mixture is agitated until all of the protein dissolves into solution and before adding any other ingredients. All the other ingredients, except the source of EGCg, the source of zinc, and food-grade acids are then added in the kettle. Before the source of EGCg, e.g., the green tea extract, is added, the pH of the blend is adjusted to the target pH, e.g., a pH of 3 to 3.5, with the food-grade acids. The solution of EGCg and zinc containing the source of the EGCg and the source of zinc are prepared in a separate kettle in the same manner as described above. The solution of EGCg and zinc is then added to the kettle containing the other ingredients and is agitated for a period of time, e.g., 5-60 minutes, to ensure homogeneous distribution of the EGCg and zinc in the composition. The agitation associated with the preparation of the solution containing EGCg and zinc, along with the addition of the EGCg and zinc solution to the kettle containing the other ingredients, may take place at 4° C. to 50° C. At this point, the liquid nutritional composition may be packaged and sterilized according to any suitable sterilization technique, such as aseptic, retort, or hot-fill sterilization.

As mentioned above, the consumption of at least one serving per day of the nutritional composition in accordance with the first, second, and fourth embodiments disclosed herein results in decreased or less skeletal muscle loss in the subject as compared to the consumption of a comparative composition containing no zinc. Skeletal muscle loss according to the first, second, and fourth embodiments disclosed herein, which is the loss of skeletal muscle mass, can be measured by any suitable known or otherwise effective technique, including, but not limited to, using urine based measurements of 3-methyl-histidine and creatinine, using a body composition analyzer, or using techniques to such as underwater or hydrostatic weighing, dual energy X-ray absorptiometry (DEXA), bioelectrical impedance, and the like, or using visual or imaging techniques such magnetic resonance imaging (MRI) or CT scans to at least in part visually determine muscle loss. The comparison of the loss of skeletal muscle in a subject that consumes the nutritional compositions disclosed herein containing EGCg and zinc to that of a subject that consumes a comparative composition containing EGCg but no zinc may not show immediate results using the aforementioned measurement techniques. The resulting effect may take days, weeks, or months of regular consumption of the nutritional compositions disclosed herein in the first, second, and fourth embodiments to obtain the stated measurable skeletal muscle loss results described above. For the purposes of determining the effects of the EGCg and zinc disclosed herein, a 3-12 month test period of regular consumption of the EGCg and zinc may be used. If the subject exhibits short term, acute loss of muscle (e.g., short term loss of muscle that requires hospitalization), a 3-5 day test period may be used.

In addition, the skeletal muscle loss, as used herein, can be measured by any suitable known or otherwise effective in vivo or in vitro technique applied to the subject, as well as applied to laboratory animals. The ubiquitin-proteasome pathway (UbP) is the major pathway of protein degradation in almost all cell types, including skeletal myotubes (in vitro) and mature skeletal muscle myofibers (in vivo). In the UbP pathway the type E3 enzymes, MURF1 and MAFBx (or Atrogin-1), can independently attach a ubiquitin moiety to specific substrate proteins to target them for degradation by the proteasome complex. Thus, MURF1, MAFBx, ubiquitin, and proteasome levels all serve as surrogate markers for protein degradation. Furthermore, during the UbP pathway process, protein is broken down, and the process ultimately yields amino acids. Thus, the increase in free amino acids present in the subject also serves as a surrogate marker for protein degradation. The increase in free amino acids occurs both in vivo and in vitro. With respect to in vivo, an increase in free amino acids present in the muscle tissue of the subject, as well as in the fluid of the subject, e.g., in serum, the bloodstream, urine, etc., is an indicator of muscle protein degradation in the subject. With respect to in vitro, for example, the increase in free amino acids released by $C_2C_{12}$ muscle myotubes serves as a marker for protein degradation. A non-limiting example of a free amino acid that acts as a marker for muscle protein degradation is 3-methyl-histidine. Further, extracellular creatine kinase is a non-limiting example of a marker associated with acute muscle protein degradation and myofiber dysfunction and atrophy.

The aforementioned techniques to measure the skeletal muscle loss in a subject also apply to the skeletal muscle function aspect of the third embodiment disclosed herein. The third embodiment is directed to a method for reducing the amount of EGCg used to preserve skeletal muscle function in a subject susceptible to loss of skeletal muscle function due to age, inactivity, or disease. In accordance with this embodiment, less EGCg is required to sustain or improve skeletal muscle function as compared to the consumption of a comparative composition containing no zinc. As mentioned above, skeletal muscle function includes at least one of skeletal muscle mass, skeletal muscle strength, and skeletal muscle quality. Thus, the skeletal muscle function as defined by skeletal muscle mass can be measured in the same manner using the same known or otherwise effective techniques as described above with respect to measuring the skeletal muscle loss of the first, second, and fourth embodiments disclosed herein. The remaining aspects of skeletal muscle function, i.e., muscle function as defined by skeletal muscle strength and skeletal muscle function as defined by skeletal muscle quality can be measured by any known or otherwise effective techniques for measuring the respective muscle function aspect.

For example, skeletal muscle strength, as defined herein, can be quantitatively measured using acute tests of maximum force, time-dependent tests of muscle endurance, time dependent tests of muscle fatigue, time dependent tests of muscle endurance and fatigue, and combinations thereof. The muscle quality of the subject, which refers to the muscle strength per the muscle volume, muscle strength per muscle cross-sectional area, or muscle strength per muscle mass, can be determined by obtaining muscle strength data for the subject as described above, and dividing the quantified muscle strength results by the measured volume or mass of the muscle at issue. The volume or mass of the muscle can be determined using any known or otherwise effective technique that provides muscle volume or mass, such as DEXA or using visual or imaging techniques such as MRI or CT scans. As discussed above with respect to the muscle loss for the first, second, and fourth embodiments disclosed herein, the comparison of the muscle function in a subject that consumes the nutritional compositions disclosed herein containing EGCg and zinc to that of a subject that consumes a comparative composition containing EGCg but no zinc may not show immediate results using the aforementioned measurement techniques. The resulting effect may take days, weeks, or months of regular consumption of the nutritional compositions disclosed herein in accordance with the fourth embodiment to obtain the stated measurable skeletal muscle function results described above. For the purposes of determining the effects of the EGCg and zinc disclosed herein for muscle function, a 3-12 month test period of regular consumption of the EGCg and zinc may be used. In the case of acute muscle loss, the resulting effect may be apparent in 3-5 days.

EXAMPLES

The following examples illustrate specific and exemplary embodiments and/or features of the methods according to the first, second, third, and fourth embodiments disclosed herein. The examples are provided solely for the purposes of illustration and should not be construed as limitations of the present disclosure. Numerous variations over these specific examples are possible without departing from the spirit and scope of the presently disclosed methods.

Example 1

Figure 1:
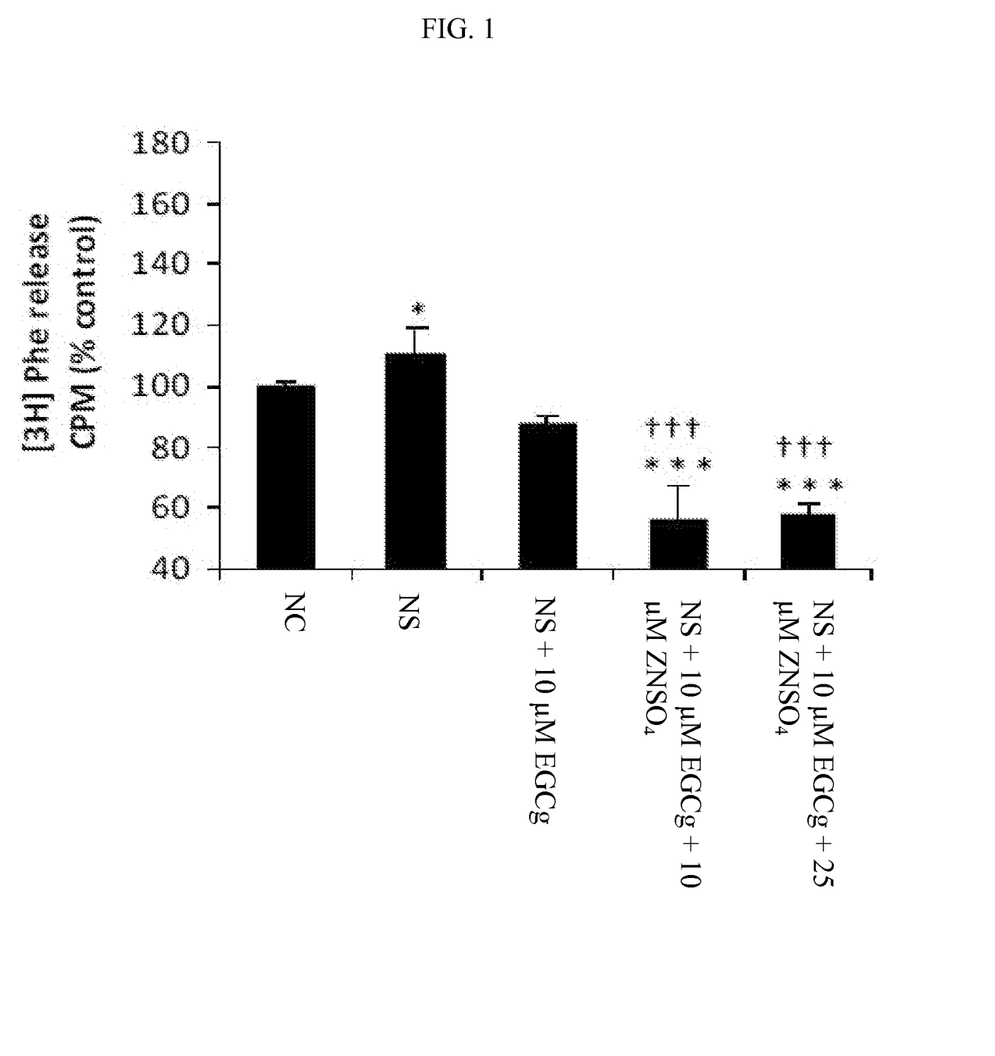
FIG. 1 shows the effect of EGCg on total protein degradation in serum starved $C_2C_{12}$ myotubes in the presence or absence of zinc.

The role of EGCg alone and EGCg in combination with zinc in preventing muscle protein degradation was evaluated in an in vitro cell-based assay using serum-starved $C_2C_{12}$ myotubes, i.e., differentiated, elongated murine myoblasts, which are routinely used to model adult skeletal myofibers in cell culture. The results of this evaluation are shown in FIG. 1. This assay measured the release of radiolabeled phenylalanine (Phe) from myotubes in response to a catabolic stimulus. Under normal growth conditions in the presence of growth factors supplied by 2% horse serum, the myotubes actively incorporated the amino acid Phe into newly synthesized muscle proteins. This is shown as the negative control for proteolysis (NC) in lane 1 of FIG. 1, i.e., the serum control. In the absence of the 2% horse serum, specifically $C_2C_{12}$ cultured in a serum-free DMEM medium, the muscle proteins began to break down, and phenylalanine was subsequently released as a free amino acid. This is shown as the serum-free, positive control for proteolysis (NS) in lane 2 of FIG. 1. FIG. 1 shows that a greater amount of Phe was released in the positive control (NS) as compared to the negative control (NC), i.e., a greater amount of protein degradation occurred in the serum-free, positive control (NS) as compared to the serum-containing negative control (NC). 10 µM EGCg was added to serum-free and serum-starved myotubes alone, i.e., lane 3 of FIG. 1. 10 µM EGCg was added to serum-free and serum-starved myotubes in combination with 10 µM of zinc sulfate, i.e., lane 4 of FIG. 1, and in combination with 25 µM of zinc sulfate, i.e., lane 5 of FIG. 1.

The addition of EGCg alone showed greater inhibition of total protein degradation as compared to each of the respective serum (NC) and serum-free (NS) controls. However, it was EGCg in combination with zinc in both lanes 4 and 5 of FIG. 1 that showed statistically significant reductions in total muscle protein degradation, as compared to the addition of EGCg alone (lane 3 of FIG. 1) and to each respective serum (NC) and serum-free (NS) controls. The experiment was replicated 2 times where n=6 over the same period of time for each sample, i.e., 24 hours for each sample. Results are expressed as mean±S.E.M and statistical analysis between groups was determined by one-way ANOVA followed by Tukey's test. The difference from negative control is indicated as *$p<0.05$, ***$p<0.001$, and †††$p<0.001$ compared with no serum.

Example 2

Figure 2:
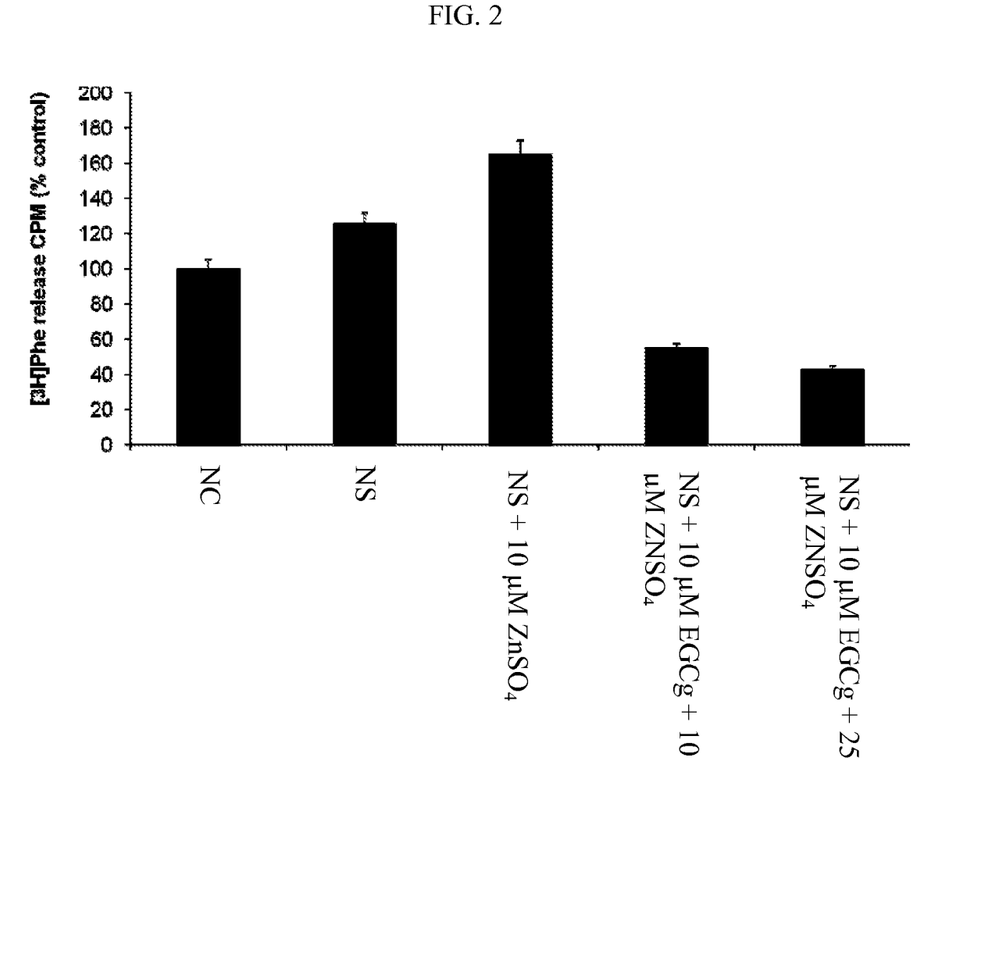
FIG. 2 shows the effect of zinc on total protein degradation in serum starved $C_2C_{12}$ myotubes in the presence or absence of EGCg.

The role of zinc alone and zinc in combination with EGCg in preventing muscle protein degradation was evaluated in an in vitro cell-based assay using serum-starved $C_2C_{12}$ myotubes, i.e., differentiated, elongated murine myoblasts, which as mentioned above are routinely used to model adult skeletal myofibers in cell culture. The results of this evaluation are shown in FIG. 2. This assay measured the release of radiolabeled phenylalanine (Phe) from myotubes in response to a catabolic stimulus. Under normal growth conditions in the presence of growth factors supplied by 2% horse serum, the myotubes actively incorporated the amino acid Phe into newly synthesized muscle proteins. This is shown as the negative control for proteolysis (NC) in lane 1 of FIG. 2, i.e., the serum control. In the absence of the 2% horse serum, specifically $C_2C_{12}$ cultured in a serum-free DMEM medium, the muscle proteins began to break down, and Phe was subsequently released as a free amino acid. This is shown as the serum-free, positive control for proteolysis (NS) in lane 2 of FIG. 2. FIG. 2 shows that a greater amount of Phe was released in the positive control (NS) as compared to the negative control (NC), i.e., a greater amount of protein degradation occurred in the serum-free, positive control (NS) as compared to the serum-containing negative control (NC). 10 µM zinc sulfate was added to serum-free and serum-starved myotubes alone, i.e., lane 3 of FIG. 2. 10 µM zinc sulfate was added to serum-free and serum-starved myotubes in combination with 10 µM of EGCg, i.e., lane 4 of FIG. 2. 25 µM of zinc sulfate was also added in combination with 10 µM of EGCg, i.e., lane 5 of FIG. 2.

The addition of zinc alone (lane 3 of FIG. 2) showed a positive correlation with total muscle Phe release, thereby showing that providing zinc alone to the myotubes promoted or increased total protein degradation as compared to each of the respective serum (NC) and serum-free (NS) controls. However, when the zinc was combined with the EGCg, i.e., in both lanes 4 and 5 of FIG. 2, statistically significant reductions in total muscle protein degradation are shown, particularly as compared to the addition of zinc alone (lane 3 of FIG. 2) and to each of the serum (NC) and serum-free (NS) controls. The experiment was replicated 2 times where n=6 over the same period of time for each sample, i.e., 24 hours for each sample. Results are expressed as mean±S.E.M and statistical analysis between groups was determined by one-way ANOVA followed by Tukey's test. The difference from negative control is indicated as *$p<0.05$, $p<0.01$, *$p<0.001$, and †††$p<0.001$ compared with no serum.

Given that the addition of zinc alone to the myotubes promotes muscle protein degradation, and given that zinc in combination with EGCg enhances the inhibition of muscle protein degradation as shown in FIGS. 1 and 2 herein, it is clear that the combination of zinc with EGCg provides an unexpected and surprising synergistic effect on mitigating skeletal muscle protein degradation.

Unless otherwise indicated herein, all sub-embodiments and optional embodiments are respective sub-embodiments and optional embodiments to all embodiments described herein. While the present application has been illustrated by the description of embodiments thereof, and while the embodiments have been described in considerable detail, it is not the intention of the applicants to restrict or in any way limit the scope of the appended claims to such detail. Additional advantages and modifications will readily appear to those skilled in the art. Therefore, the application, in its broader aspects, is not limited to the specific details, the representative apparatus, and illustrative examples shown and described. Accordingly, departures may be made from such details without departing from the spirit or scope of the applicant's general inventive concept.

To the extent that the term "includes" or "including" is used in the specification or the claims, it is intended to be inclusive in a manner similar to the term "comprising" as that term is interpreted when employed as a transitional word in a claim. Furthermore, to the extent that the term "or" is employed (e.g., A or B) it is intended to mean "A or B or both." When the applicants intend to indicate "only A or B but not both" then the term "only A or B but not both" will be employed. Thus, use of the term "or" herein is the inclusive, and not the exclusive use. See Bryan A. Garner, *A Dictionary of Modern Legal Usage* 624 (2d. Ed. 1995). Also, to the extent that the terms "in" or "into" are used in the specification or the claims, it is intended to additionally mean "on" or "onto." Furthermore, to the extent the term "connect" is used in the specification or claims, it is intended to mean not only "directly connected to," but also "indirectly connected to" such as connected through another component or components.

The invention claimed is:

1. A method for enhancing the efficacy of epigallocatechin gallate (EGCg) in mitigating skeletal muscle loss in a subject in need thereof or for reducing the amount of epigallocatechin gallate (EGCg) required to decrease skeletal muscle loss due to aging, inactivity, or disease in a subject in need thereof, the method comprising:
provamount of ing to the subject in need thereof at least one serving per day of a nutritional composition, the nutritional composition comprising:
at least one source of EGCg in an amount sufficient to provide 10-1000 mg of EGCg per serving;
at least one source of zinc in an amount sufficient to provide 2.5-30 mg of zinc per serving; and
at least one source of protein in an amount sufficient to provide 5-50 g of protein per serving;
whereby consumption of at least one serving per day of the nutritional composition results in decreased skeletal muscle loss in the subject as compared to the consumption of a comparative composition containing no zinc.

2. The method of claim 1, wherein the nutritional composition is a liquid nutritional product having a serving size ranging from 150 mL to 500 mL.

3. The method of claim 1, wherein the total amount of EGCg per serving is 125-500 mg and the total amount of zinc per serving is 5-20 mg.

4. The method of claim 1, wherein the at least one source of EGCg comprises green tea extract that contains 30-100 weight % of EGCg.

5. The method of claim 1, wherein the at least one source of EGCg further comprises at least one of a catechin (C), a gallocatechin (GC), an epicatechin (EC), an epicatechin gallate (ECg), an epigallocatechin (EGC), and combinations thereof.

6. The method of claim 1, wherein the at least one source of zinc is a zinc salt selected from the group consisting of zinc sulfate, zinc gluconate, zinc iodide, zinc chloride, zinc citrate, zinc carbonate, zinc hydroxide, zinc lactate, zinc acetate, zinc fluoride, zinc bromide, zinc sulfonate, zinc glucuronate, and combinations thereof.

7. The method of claim 1, wherein the at least one source of protein is selected from the group consisting of whey protein concentrates, whey protein isolates, whey protein hydrolysates, acid caseins, sodium caseinates, calcium caseinates, potassium caseinates, casein hydrolysates, milk protein concentrates, milk protein isolates, milk protein hydrolysates, nonfat dry milk, condensed skim milk, soy protein concentrates, soy protein isolates, soy protein hydrolysates, pea protein concentrates, pea protein isolates, pea protein hydrolysates, collagen proteins, and combinations thereof.

8. The method of claim 1, wherein the nutritional composition further comprises an ingredient selected from the group consisting of at least one source of carbohydrates, at least one source of fat, and combinations thereof.

9. The method of claim 1, wherein the nutritional composition has a calorie content of 50-500 kcal per serving.

10. The method of claim 1, wherein the nutritional composition is a clear liquid nutritional product having a pH of 2-5 and having no more than 0.5 weight % fat based on the total weight of the nutritional composition.

11. The method of claim 1, wherein the nutritional composition is a liquid nutritional product and further comprises at least one source of carbohydrates and at least one source of fat, and wherein per serving:
the at least one source of protein provides 10-50% of the calories,
the at least one source of carbohydrates provides 20-85% of the calories, and
the at least one source of fat provides 5-50% of the calories.

12. The method of claim 1, wherein the glycemic index of the nutritional composition is less than or equal to 50.

13. The method of claim 1, whereby administration of at least one serving per day of the nutritional composition results in sustained or improved muscle function in the subject as compared to the administration of a comparative composition containing no zinc.

14. The method of claim 1, wherein the nutritional composition further comprises at least one source of a compound selected from the group consisting of leucine, isoleucine, valine, glycine, histidine, lysine, methionine, phenylalanine, threonine, tryptophan, carnitine, carnosine, creatine, alpha-ketoisocaproate, and combinations thereof.

15. The method of claim 1, wherein the nutritional composition further comprises at least one source of a compound selected from the group consisting of beta-hydroxy-beta-methylbutyrate, beta-alanine, and combinations thereof.

16. The method of claim 1, wherein the molar ratio of zinc to EGCg ranges from 0.1:1 to 2:1.

17. A method for reducing the amount of epigallocatechin gallate (EGCg) needed to mitigate skeletal muscle loss attributable to aging, inactivity, or disease in a subject in need thereof, the method comprising:
providing a serving of a liquid nutritional composition to the subject at least once a day, the nutritional composition including the following ingredients based on a 150 mL to 500 mL serving size:
at least one green tea extract in an amount sufficient to provide 10-1000 mg of EGCg per serving;
at least one source of zinc in an amount sufficient to provide 2.5-30 mg of zinc per serving; and
at least one source of protein in an amount sufficient to provide 5-50 g of protein per serving,
whereby consumption of the nutritional composition results in less skeletal muscle loss in the subject as compared to the consumption of a comparative composition containing no zinc.

18. A method for reducing the amount of epigallocatechin gallate (EGCg) required to sustain or improve skeletal muscle function in a subject in need thereof, due to age, inactivity, or disease, the method comprising:
providing to the subject a nutritional composition containing a combination of 10-1000 mg of EGCg and 2.5-30 mg of zinc,
whereby consumption of the nutritional composition requires less EGCg to sustain or improve skeletal muscle function as compared to the consumption of a comparative composition containing no zinc.

19. The method of claim 18 comprising providing at least one serving per day of the nutritional composition to the subject, wherein the nutritional composition is a liquid nutritional composition having a serving size ranging from 150 mL to 500 mL.

20. The method of claim 18, wherein the nutritional composition includes an ingredient selected from the group consisting of at least one source of protein, at least one source of carbohydrates, at least one source of fat, and combinations thereof, and
wherein the nutritional composition has a calorie content of 50-500 kcal per serving.

* * * * *